(12) United States Patent
Rovison, Jr. et al.

(10) Patent No.: US 9,320,820 B2
(45) Date of Patent: Apr. 26, 2016

(54) STERILIZATION METHOD

(71) Applicant: PEROXYCHEM LLC, Philadelphia, PA (US)

(72) Inventors: John M. Rovison, Jr., Sanborn, NY (US); Shibu Abraham, Stewartsville, NJ (US); Charles J. Lymburner, Tonawanda, NY (US); Michael J. Digeronimo, Chester, NY (US)

(73) Assignee: PeroxyChem LLC, Philadelphia, PA (US)

( * ) Notice: Subject to any disclaimer, the term of this patent is extended or adjusted under 35 U.S.C. 154(b) by 0 days.

(21) Appl. No.: 14/251,888

(22) Filed: Apr. 14, 2014

(65) Prior Publication Data

US 2015/0050184 A1 Feb. 19, 2015

Related U.S. Application Data

(63) Continuation of application No. 12/697,660, filed on Feb. 1, 2010, now Pat. No. 8,696,986.

(60) Provisional application No. 61/206,596, filed on Feb. 2, 2009.

(51) Int. Cl.
| | |
|---|---|
| *A61L 9/00* | (2006.01) |
| *F26B 3/00* | (2006.01) |
| *A61L 2/20* | (2006.01) |

(52) U.S. Cl.
CPC . *A61L 2/20* (2013.01); *A61L 2/208* (2013.01); *A61L 2202/23* (2013.01); *A61L 2202/24* (2013.01)

(58) Field of Classification Search
CPC ........... A61L 2/00; A61L 2/186; A61L 2/208; A61L 2/22; A61L 2/07
USPC .................. 422/1, 4, 28–29, 32, 123; 134/31; 34/443
See application file for complete search history.

(56) References Cited

U.S. PATENT DOCUMENTS

| | | |
|---|---|---|
| 5,645,796 A | 7/1997 | Caputo et al. |
| 6,036,918 A | 3/2000 | Kowanko |
| 6,261,518 B1 | 7/2001 | Caputo et al. |
| 6,475,435 B1 | 11/2002 | Taggart |
| 6,596,231 B1 * | 7/2003 | Catelli et al. ............ 422/28 |
| 6,790,380 B2 | 9/2004 | Sato et al. |
| 7,186,374 B2 | 3/2007 | Zelina et al. |
| 7,569,180 B2 | 8/2009 | Kohler |
| 7,790,104 B2 | 9/2010 | Adams et al. |
| 2002/0085971 A1 | 7/2002 | Raniwala |
| 2003/0230567 A1 | 12/2003 | Centanni et al. |
| 2005/0025665 A1 | 2/2005 | Raniwala |
| 2005/0175500 A1 | 8/2005 | Adams et al. |
| 2007/0274858 A1 | 11/2007 | Childers et al. |
| 2008/0267818 A1 | 10/2008 | Hill |

FOREIGN PATENT DOCUMENTS

| | | |
|---|---|---|
| DE | 3523310 A1 | 1/1987 |
| JP | 2003181404 A | 7/2003 |

OTHER PUBLICATIONS

Supplementary European Search Report, Application No. 10736519. 9-2113/2391391, PCT/US2010022718, dated Jan. 21, 2013.
Lerouge S. et al. "Plasma Sterilization; a Review of Parameters, Mechanisms and Limitations". Plasmas and Polymers Sep. 2001, vol. 6, No. 3, pp. 175-188.
Porter, Dorothy M. et al. "Sporicidal Effect of Peracetic Acid Vapor". Applied Microbiology, Nov. 1968, vol. 16, No. 11, pp. 1782-1785.
Examination Report issued on Aug. 6, 2015 for corresponding EP Application No. 10736519.9.

* cited by examiner

*Primary Examiner* — Monzer R Chorbaji
(74) *Attorney, Agent, or Firm* — Duane Morris LLP

(57) ABSTRACT

A method of sterilizing a material, said method comprising the steps of: (a) introducing a solution comprising peroxyacetic acid into a hot gaseous stream to produce a peroxyacetic acid vapor; and (b) contacting such peroxyacetic acid vapor with the material to be sterilized.

12 Claims, No Drawings

STERILIZATION METHOD

CROSS REFERENCE TO RELATED APPLICATIONS

This application is a Continuation of U.S. application Ser. No. 12/697,660, filed Feb. 1, 2010, which claims the benefit of the filing date of U.S. Provisional Application No. 61/206,596, which was filed Feb. 2, 2009. The entire content of these applications is hereby incorporated by reference herein.

FIELD OF THE INVENTION

The present invention is directed to a method of sterilizing a surface employing a vapor comprising peroxyacetic acid. This vapor is created by introducing a solution comprising diluted peroxyacetic acid solution into a hot gaseous stream. The use of such a true vapor results in the desirable sterilization of a substrate without the deposition of condensate droplets onto its surface.

BACKGROUND OF THE INVENTION

The necessity of sterilizing surfaces for health and sanitary purposes has long been recognized. Effective sterilization processes are needed for a variety of purposes including aseptic packaging, medical instrument sterilization, biocidal vector environmental remediation, fumigation, vessel sterilization, food stuff treatments, and others.

Among the compounds known in the art which are useful for bacterial sterilization is peroxyacetic acid. Typically, peroxyacetic acid is employed in aqueous-based systems as an equilibrium mixture comprising peracetic acid, acetic acid, and hydrogen peroxide. While such systems have been shown to be effective, in many instances a separate rinsing and/or drying step is required. This can add considerable expense and time to the sterilization process, particularly when the substrate may be adversely affected by high temperatures needed to expedite the drying process.

It would therefore be highly desirable to possess a method for using peroxyacetic acid as a sterilizing agent which method did not require an energy intensive or time delaying drying step.

SUMMARY OF THE INVENTION

The present invention is directed to a method of sterilizing a material, said method comprising the steps of:

a) introducing a solution comprising peroxyacetic acid into a hot gaseous stream to produce a peroxyacetic acid vapor; and b) contacting such peroxyacetic acid vapor with the material to be sterilized.

This method permits the effective sterilization of a material without the need for a subsequent drying step as solution droplets are not formed and not deposited upon the surface of the material so treated. Accordingly, a wide variety of materials may be rapidly and economically sterilized employing the method of this invention.

DETAILED DESCRIPTION OF THE INVENTION

The present invention is directed to a method of sterilizing a material, said method comprising the steps of:

a) introducing a solution comprising peroxyacetic acid into a hot gaseous stream to produce a peroxyacetic acid vapor; and b) contacting such peroxyacetic acid vapor with the material to be sterilized.

As is employed herein, the term vapor intended to mean a state in which the peroxyacetic acid is substantially entirely in the gaseous form. This is in contrast to mist or fog, both of which contain a significant proportion of liquid droplets suspended in the air. Unlike the use of a mist or fog, it has been found the use of peroxyacetic acid in vapor form provides excellent sterilization of materials without the concomitant formation of water droplets on the material surface.

Peroxyacetic acid is typically employed in the form of an aqueous equilibrium mixture of acetic acid, hydrogen peroxide and peroxyacetic acid. [ratios of 35:10:15]. Such composition may typically further comprise stabilizers such as phosphonic acids or phosphonates, i.e. Degquest 2010 or sequestriants such as dipicolinic acid, as well as other ingredients such as: mineral acid catalysts (sulfuric, nitric, or phosphoric acids); surfactants such as anionic laurylates, sorbitans and their respective esters, i.e. polyethylene sorbitan monolaurylates; and short chain fatty esters (C6-C12) forming mixed peracids in solution.

Prior to introduction into the heated gas stream, the peroxyacetic acid is preferably diluted, by the addition of water, to a concentration of less than about 10,000 ppm, preferably of less than about 4,000 ppm.

The heated gas stream is typically sterile air, although other gases such as nitrogen, $CO_2$, or inert noble gas carriers may also be employed. Such gas stream is typically heated to a temperature of at least about 300° C., preferably to a minimal temperature of about 250° C. and can be in excess of 350° C. providing it can be cooled sufficiently for application. It then is typically cooled to between about 80° C. and about 120° C. prior to the introduction of the peroxyacetic acid solution. The heated gas stream at the point of peroxyacetic acid should have a temperature of at least 5° C. higher than the dew point of peroxyacetic acid (ca. 46.5°-49.9° C.); i.e., of at least about 55° C., in order to ensure that the peroxyacetic acid is converted into a vapor rather than a fog or mist.

The peroxyacetic acid may be introduced into the heated air stream by any means well known to one of skill in the art. One preferred method is by direct injection of a solution.

The peroxyacetic acid vapor is then contacted with the material to be sterilized for a period sufficient to kill the contaminants of concern. This time period will vary according to variables such as the concentration of the peroxyacetic acid vapor employed; the nature of the surface of the material to be sterilized; the particular contaminants to be sterilized; the concentration of the contaminants to be sterilized; and the like. Typically, such contact will maintained for a period of between about 15 and about 40 minutes.

A wide variety of materials may be sterilized employing the method of this invention, including hard surfaces of metals, plastics, polymers, and elastomers.

The present method may be used to sterilize materials contaminated with those bacteria typically controlled by peroxyacetic acid in the liquid form. These include bacteria and spores of the genus *Bacillus* using *B. thuringiensis* and *B. atrophaeus* as surrogates for more pathogenic species (forms) such as *C. botulinum* as well as more typical genera of bacteria, fungi, and viruses and protozoans often controlled by PAA such as (but not limited to): *Staphlococcus, Enterococcus, Salmonella, Capmylobacter, Pseudomonas, Candida, Rhizopus, Mucor, Influenza* etc.

The following Example is presented to offer further illustration of the method of this invention.

EXAMPLE

Employing a DA 2000 aseptic pouch filler, 1.5 Liters of a diluted solution of peroxyacetic acid (having a concentration of 4000 PPM) were injected over a period of 17 minutes into a sterile air stream which had been heated to 300° C. and allowed to cool to 90° C. No misting, fog or condensate was observed, indicating that full vaporization had occurred. Coupons inoculated with the spore-forming organisms listed at the concentrations listed were placed within the machine "head" sterile areas and exposed to the peroxyacetic acid vapor. No condensate was observed on any of the coupons tested. Upon completion of the injection of the peroxyacetic acid solution, the coupons were immediately removed from the machine. Samples were taken from the coupons and transferred to appropriate growth media, cultured, and monitored for growth. The results of such testing are summarized in Table 1.

TABLE 1

| Test # | Organism | Organism Concentration | Total Sites | No Growth | Growth |
|---|---|---|---|---|---|
| 1 | *B. thuringiensis* | $7.5 \times 10^4$ | 70 | 70 | 0 |
| 2 | *B. thuringiensis* | $7.5 \times 10^4$ | 70 | 70 | 0 |
| 3 | *B. thuringiensis* | $4.5 \times 10^5$ | 70 | 70 | 0 |
| 4 | *B. thuringiensis* | $4.5 \times 10^5$ | 70 | 69 | 1 |
| 5 | *B. thuringiensis* | $3.5 \times 10^6$ | 70 | 69 | 1 |
| 6 | *B. thuringiensis* | $3.5 \times 10^6$ | 70 | 68 | 2 |
| 7 | *B. atrophaeus* | $3.1 \times 10^4$ | 9 | 9 | 0 |
| 8 | *B. atrophaeus* | $3.1 \times 10^4$ | 9 | 9 | 0 |
| 9 | *B. atrophaeus* | $2.0 \times 10^5$ | 9 | 9 | 0 |
| 10 | *B. atrophaeus* | $2.0 \times 10^5$ | 9 | 9 | 0 |

The above results demonstrate the excellent activity demonstrated by the peroxyacetic acid vapor employed in the method of this invention.

What is claimed is:

1. A method of sterilizing a material, said method comprising the steps of:

a) introducing a solution comprising peroxyacetic acid into a hot gaseous stream to produce a peroxyacetic acid vapor; and b) contacting such peroxyacetic acid vapor with the material to be sterilized without the deposition of condensate droplets onto the surface of such material.

2. The method of claim 1 wherein such material is selected from the group consisting of metals, plastics, polymers and elastomers.

3. The method of claim 1 wherein the peroxyacetic acid is diluted to a concentration of less than 10,000 ppm prior to being introduced into the hot gaseous stream.

4. The method of claim 3 wherein the peroxyacetic acid is diluted to a concentration of less than 4,000 ppm prior to being introduced into the hot gaseous stream.

5. The method of claim 1 wherein the hot gaseous stream is sterile air.

6. The method of claim 1 wherein the hot gaseous stream is selected from the group consisting of nitrogen, carbon dioxide and noble gases.

7. The method of claim 1 wherein the hot gaseous stream is heated to a temperature of about 300° C. prior to the introduction of the peroxyacetic acid.

8. The method of claim 1 wherein the hot gaseous stream is heated to a temperature of about 300° C. and is then cooled to a temperature of between about 80° C. and about 120° C. prior to the introduction of the peroxyacetic acid.

9. The method of claim 1 wherein the temperature of the hot gaseous stream is at least about 5° C. higher than the dew point of peroxyacetic acid.

10. The method of claim 1 wherein the contact between the peroxyacetic acid vapor and the material to be sterilized is maintained for a period of between about 15 and about 40 minutes.

11. The method of claim 1, wherein the material to be sterilized is at risk for contamination with a sporulating microorganism.

12. The method of claim 1, wherein the sporulating microorganism comprises *Clostridium* spp.

* * * * *